US010398569B2

(12) United States Patent
Jaumard (10) Patent No.: US 10,398,569 B2
(45) Date of Patent: Sep. 3, 2019

(54) IMPACTOR-EXTRACTOR

(71) Applicant: Zimmer, Inc., Warsaw, IN (US)

(72) Inventor: Nicolas V. Jaumard, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 274 days.

(21) Appl. No.: 15/617,410

(22) Filed: Jun. 8, 2017

(65) Prior Publication Data

US 2018/0028249 A1 Feb. 1, 2018

Related U.S. Application Data

(60) Provisional application No. 62/366,683, filed on Jul. 26, 2016.

(51) Int. Cl.
| | |
|---|---|
| *A61B 17/92* | (2006.01) |
| *A61F 2/46* | (2006.01) |
| *A61F 2/30* | (2006.01) |

(52) U.S. Cl.
CPC ............ *A61F 2/4607* (2013.01); *A61B 17/92* (2013.01); *A61B 17/921* (2013.01); *A61F 2/4601* (2013.01); *A61F 2002/30616* (2013.01); *A61F 2002/4619* (2013.01); *A61F 2002/4627* (2013.01); *A61F 2002/4628* (2013.01); *A61F 2002/4681* (2013.01)

(58) Field of Classification Search
CPC .... A61F 2/4607; A61F 2/4601; A61B 17/921; A61B 17/92
See application file for complete search history.

(56) References Cited

U.S. PATENT DOCUMENTS

| | | | |
|---|---|---|---|
| 2003/0050706 A1* | 3/2003 | Draenert | A61F 2/36 623/23.23 |
| 2014/0142583 A1* | 5/2014 | Fortin | A61B 17/1604 606/100 |
| 2014/0276850 A1* | 9/2014 | Chaney | A61B 17/164 606/84 |

* cited by examiner

*Primary Examiner* — Christian A Sevilla
(74) *Attorney, Agent, or Firm* — Schwegman Lundberg & Woessner, P.A.

(57) ABSTRACT

An impactor-extractor for inserting or extracting a stem of a prosthesis into or from a bone can include a body having a first end and a second end. The body can include an impact head located at the first end. A lever can be connected to the body and pivotable about a first pivot point distal to the first end of the body. A base can be located at the second end of the body and can include a first taper connector sized to mate with a second taper connector of the stem. A lock can be located at and pivotable about a second pivot point proximate the second end and can include an extension configured to secure the stem to the first taper connector. Linkages can connect the lever and the lock.

20 Claims, 5 Drawing Sheets

IMPACTOR-EXTRACTOR

RELATED APPLICATIONS

The application claims the benefit of priority to U.S. Provisional Application Ser. No. 62/366,683, filed Jul. 26, 2016, the content of which is incorporated herein by reference in its entirety.

FIELD OF THE DISCLOSURE

The present disclosure relates to surgical implant systems, including implants, instruments, and methods for installing and extracting an implant.

BACKGROUND

A prosthesis or implant can be positioned in an anatomy, such as a human patient, for various purposes. For example, a prosthesis can be positioned to replace an articulating portion of an anatomy. An incorrectly installed stem can result in an incorrectly placed prosthesis. An incorrectly placed prosthesis can result in pain, limit range of motion, increase wear debris, limit joint stability, and decrease the lifespan of the prosthesis.

SUMMARY

To better illustrate the system disclosed herein, a non-limiting list of examples is provided here:

Example 1 can include an impactor-extractor for inserting or extracting a stem of a prosthesis into or from a bone. The impactor-extractor can comprise a body, a lever, a base, a lock, and linkages. The body can have a first end and a second end. The body can include an impact head located at the first end of the body. The lever can be connected to the body. The lever can be pivotable about a first pivot point distal to the impact head of the body. The base can be located at the second end of the body. The base can include a first taper connector sized to mate with a second taper connector of the stem. The lock can be located at and pivotable about a second pivot point proximate the second end. The lock can include an extension configured to secure the stem to the first taper connector. The linkages can connect the lever and the lock. Movement of the lever in a first direction can cause the lock to pivot about the second pivot point and the extension to engage the stem. Movement of the lever in a second direction can cause the lock to pivot about the second pivot point and the extension to disengage the stem.

In Example 2, the impactor-extractor of Example 1 can optionally include the first taper connector being a male taper and the second taper connector being a female taper.

In Example 3, the impactor-extractor of Example 1 can optionally include the first taper connector being a female taper and the second taper connector being a male taper.

In Example 4, the impactor-extractor of Example 1 can optionally include the extension including a protrusion sized to be received within an indentation formed in the stem.

In Example 5, the impactor-extractor of any one of or any combination of Examples 1-4 can optionally include a sleeve sized to fit over the first taper and into the second taper.

In Example 6, the impactor-extractor of Example 5 can optionally include the sleeve being selected from a plurality of sleeves. Each of the plurality of sleeves configured to mate with stems of differing sizes.

In Example 7, the impactor-extractor of any one of or any combination of Examples 1-5 can optionally include the base being selected from a plurality of bases. Each of the plurality of bases configured to mate with stems of differing sizes.

In Example 8, the impactor-extractor of any one of or any combination of Examples 1-7 can optionally include the linkage resting within the body.

In Example 9, the impactor-extractor of any one of or any combination of Examples 1-7 can optionally include the impact head including a proximal surface and a distal surface. The proximal surface for receiving an impaction force to seat the stem within a canal of the bone. The distal surface for receiving an extraction force to unseat the stem from the canal of the bone.

In Example 10, the impactor-extractor of any one of or any combination of Examples 1-4 can optionally include the base including a baseplate located between the first taper and the body. The baseplate configured to disperse an impaction force over a surface of the stem.

In Example 11, the impactor-extractor of Example 10 can optionally include a sleeve sized to fit over the first taper and a contact surface of the baseplate and into the second taper.

Example 12 can include an impactor-extractor for inserting or extracting a stem of a prosthesis into or from a bone. The impactor-extractor can comprise a body, a lever, a base, a lock, and linkages. The body can have a first end and a second end. The body can include an impact head located at the first end of the body. The body can have a curved profile such that a distal surface of the impact head is offset from the second end and normal to an axis of the stem. The lever can be connected to the body. The lever can be pivotable about a first pivot point. The base can be located at the second end of the body. The base can include a first taper sized to be received by a second taper of the stem. The lock can be located at and pivotable about a second pivot point proximate the second end. The lock can include a protrusion sized to be received within an indentation formed in the stem. The linkages can connect the lever and the lock. Movement of the lever in a first direction can cause the lock to pivot about the second pivot point and the protrusion to engage the indentation. Movement of the lever in a second direction can cause the lock to pivot about the second pivot point and the protrusion to disengage the indentation.

In Example 13, the impactor-extractor of Example 12 can optionally include the first taper connector being a male taper and the second taper connector being a female taper.

In Example 14, the impactor-extractor of Example 12 can optionally include the first taper connector being a female taper and the second taper connector being a male taper.

In Example 15, the impactor-extractor of one of or any combination of Examples 12-14 can optionally include the base including a baseplate located between the first taper and the body. The baseplate configured to disperse an impaction force over a surface of the stem.

In Example 16, the impactor-extractor of Example 12 can optionally include a sleeve sized to fit over the first taper and a contact surface of the baseplate and into the second taper.

In Example 17, the impactor-extractor of Example 12 can optionally include a sleeve sized to fit over the first taper and be received within the second taper.

In Example 18, the impactor-extractor of any one of Examples 16 and 17 can optionally include the sleeve being selected from a plurality of sleeves, each of the plurality of sleeves configured to mate with stems of differing sizes.

In Example 19, the impactor-extractor of any one of or any combination of Examples 12-18 can optionally include the linkage resting within the body.

In Example 20, the impactor-extractor of Example 12 can optionally include the impact head further including a proximal surface and a distal surface. The proximal surface for receiving an impaction force to seat the stem within a canal of the bone and the distal surface for receiving an extraction force to unseat the stein from the canal of the bone.

In Example 21, the impactor-extractor of any one of or any combination of Examples 12-17 and 20 can optionally include the base being selected from a plurality of bases. Each of the plurality of bases configured to mate with stems of differing sizes.

Example 22 can include a method of implanting a stem of a prosthesis into a bone of a patient. The method can comprise resecting a head of the bone; reaming a canal within the bone; inserting a first taper of an impactor-extractor into a second taper of the stem; rotating a lever from a first position on a body of the impactor-extractor to a second position on the body of the impactor-extractor, wherein rotating the lever causes a lock to pivot about a pivot point located proximate the first taper such that an extension of the lock engages the stem; inserting the stem into the canal within the bone; and impacting a distal surface of an impaction head of the body to seat the stem into the canal.

In Example 23, the method of Example 22 can optionally include extracting he stem from the canal.

In Example 24, extracting the stem from the canal in Example 23 can optionally include inserting the first taper of the impactor-extractor into the second taper of the stem; rotating the lever from the first position on the body to the second position on the body, wherein rotating the lever causes the lock to pivot about the pivot point located proximate the first taper such that the extension of the lock engages the stem; and impacting a proximal surface of the impaction head of the body to unseat the stem from the canal.

In Example 25, the method of any one of or any combination of Examples 22-24 can optionally include the head being a humeral head and the bone being a humerus.

In Example 26, the method of any one of or any combination of Examples 22-24 can optionally include the head being a femoral head and the bone being a femur.

In Example 27, the method of any one of or any combination of Examples 22-26 can optionally include the first taper connector being a male taper and the second taper connector being a female taper.

In Example 28, the method of any one of or any combination of Examples 22-26 can optionally include the first taper connector being a female taper and the second taper connector being a male taper.

In Example 29, the impactor-extractors or methods of any one of or any combination of Examples 1-28 is optionally configured such that all elements or options recited are available to use or select from.

BRIEF DESCRIPTION OF THE FIGURES

The above-mentioned and other features and advantages of this disclosure, and the manner of attaining them, will become more apparent and the disclosure itself will be better understood by reference to the following description of embodiments taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

As used herein, the following directional definitions apply. Anterior and posterior mean nearer the front or nearer the rear of the body, respectively, proximal and distal mean nearer to or further from the root of a structure, respectively, and medial and lateral mean nearer the sagittal plane or further from the sagittal plane, respectively. The sagittal plane is an imaginary vertical plane through the middle of the body that divides the body into right and left halves. In addition, the terms implant and prosthesis, and variations thereof, can be used interchangeably.

Patients can suffer from various inflictions that can cause a need for a joint to be replaced. For example, a patient can suffer from arthritis or suffer an injury that can be repaired with a joint replacement. In one example, a stem of a prosthesis can be inserted into a bone. For instance, during a hip replacement procedure a stem can be installed, permanently or temporarily, into a resected femur. In a shoulder replacement procedure, a stem can be installed, permanently or temporarily, into a resected humerus.

In addition to installation, stems can be removed. For example, a previously installed prosthesis can be replaced or revised. Furthermore, during installation of a prosthesis a temporary stem can be installed in order to, for example, test placement and determine proper offsets and other parameters for the permanent prosthesis. In either case, a stem may need to be removed.

As disclosed herein, an impactor-extractor can be used to both install and remove a stem. The impactor-extractor can be sized and shaped to correspond to various anatomy and. surgical procedures. For example, an impactor-extractor for use in a shoulder replacement procedure can be a different size and shape than an impactor-extractor for use in a hip replacement procedure. In addition, an impactor-extractor for a hip or shoulder replacement procedure can have a curved profile to assist with anterior or posterior surgical approaches as necessary.

As disclosed herein, the impactor-extractor can be connected to a portion of the implant such as a stem. The impactor-extractor can include an impact head. During surgery, a surgeon can impact a distal surface of the impact head to seat the implant. Also as discussed herein, the surgeon can impact a proximal surface of the impact head to unseat the implant.

Figure 1:
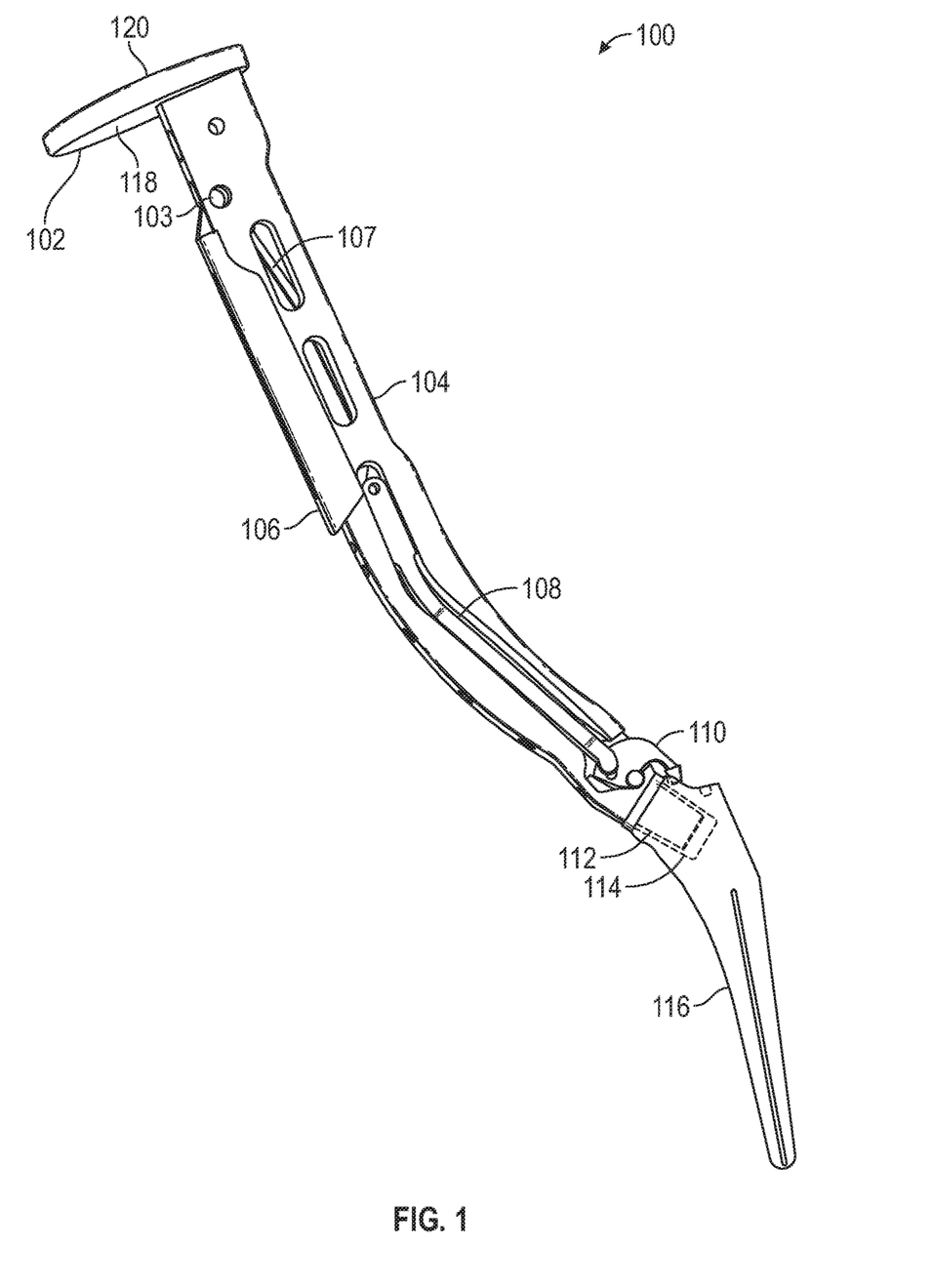
FIG. 1 shows an example of an impactor-extractor in accordance with at least one example of the present disclosure.

Turning now to the figures, FIG. 1 shows an impactor-extractor 100 in accordance with at least one example disclosed herein. The impactor-extractor 100 can include an impact head 102, a body 104, a lever 106, linkages 107 and 108, a lock 110, and a first taper 112. As shown in FIG. 1, the first taper 112 can be inserted into a second taper 114 of a stem 116. The first taper 112 can include a male taper and the second taper 114 can include a female taper. The first taper 112 and the second taper 114 can include, but are not limited to, conical tapers, square tapers, cylindrical tapers, etc. The stem 116 can be a femoral stem, a humeral stem, or any other component of an implant that needs to be installed in a patient.

Once the stem 116 is connected to the impactor-extractor 100, the stem 116 can be installed or extracted from a bone (not shown). For example, the impact head 102 can include a proximal surface 118 and a distal surface 120. During installation of the stem 116, a surgeon can impact the distal surface 120 with an appropriate tool. The impact force can be transmitted by the body 104 into the stem 116 to seat the stem 116 into the bone.

Prior to impacting the distal surface 120, the surgeon can use the impactor-extractor 100 to position the stem 116. For example, with the stem 116 connected to the impactor-extractor 100, the surgeon can use the impactor-extractor 100 to maneuver the stem 116. The surgeon can utilize the impactor-extractor 100 to twist, pry, or otherwise manipulate the stem 116. The impactor-extractor 100 can provide leverage to assist the surgeon in positioning the stem 116.

To remove the stem 116, the surgeon can impact the proximal surface 118 with the appropriate tool. The impact force can be transmitted by the body 104 and the lock 110 to the stem 116 and can unseat the stem 116 from the bone. Once the stem 116 is unseated from the bone, the surgeon can utilize the impactor-extractor 100 to manipulate the stem 116. For instance, once the stem 116 is unseated, the surgeon can utilize the impactor-extractor 100 to pull the stem 116 from the bone without having to grip the stem 116 with other tools or his or her hands.

Figure 2:
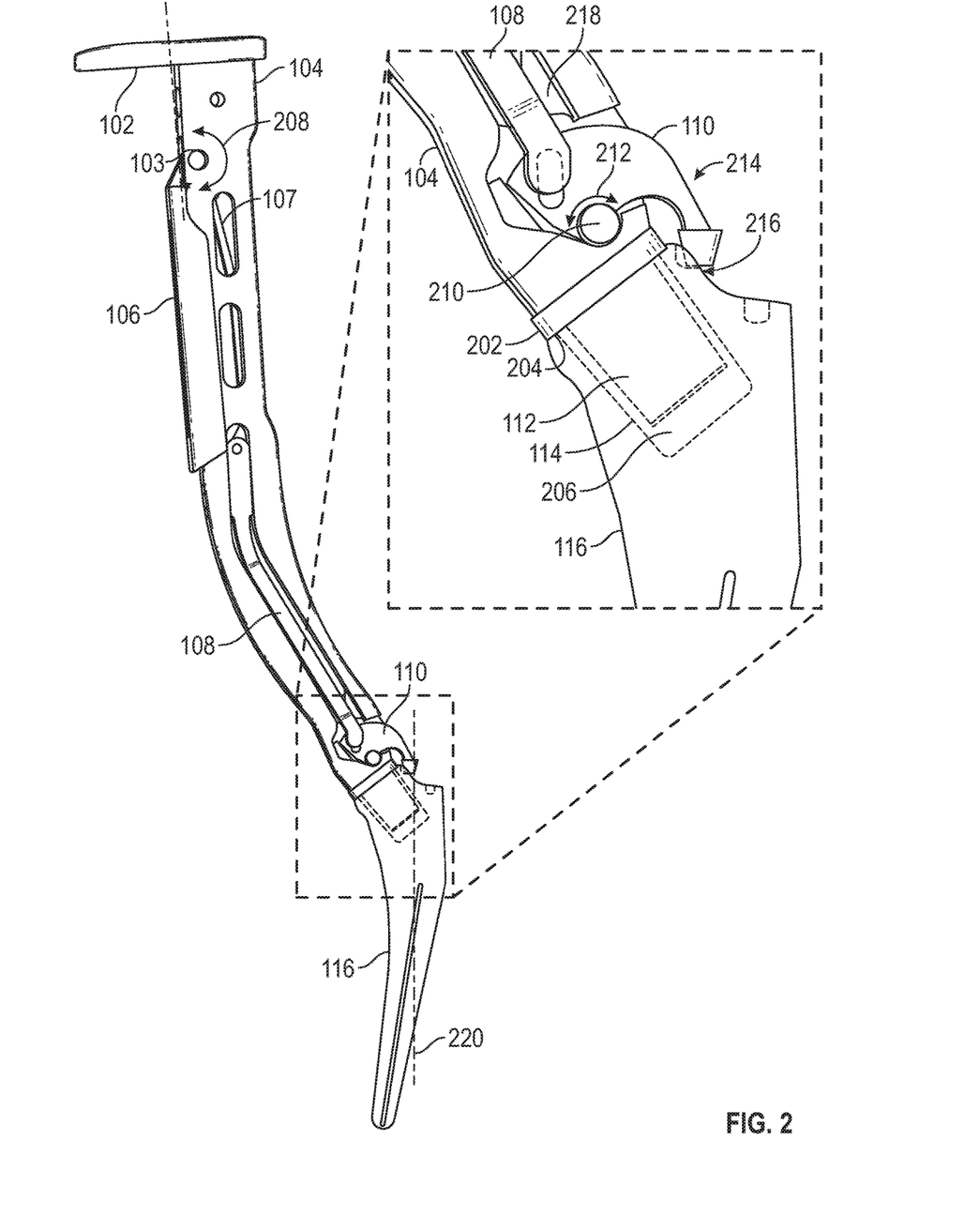
FIG. 2 shows an example of an impactor-extractor in accordance with at least one example of the present disclosure.

FIG. 2 shows the impactor-extractor 100 and details regarding connecting the stem 116 to the impactor-extractor 100 in accordance with at least one example disclosed herein. As shown in FIG. 2, the impact head 102 can be located at a first end of the body 104 and a base 202. can be located at a second end of the body 104. The base 202 can include the first taper 112. The base 202 can provide a contact surface 204 that can contact the stem 116. During installation of the stem 116, the contact surface 204 can distribute the impact force over a greater surface area of the stem 116. The distribution of the impact force can aid in hindering the impactor-extractor 100 from marring a surface of or otherwise damaging the stem 116.

In addition, a sleeve 206 can be sized to fit over the first taper 112 and into the second. taper 114. The sleeve 206 can also cover the contact surface 204. The sleeve 206 can be made of a polymer or other material that can protect the first taper 112, the second taper 114, and the stem 116. The sleeve 206 can be selected from a plurality of sleeves. For example, the base 202 can be permanently fixed to the body 104. For instance, the base 202 can be welded to the body 104 or the base 202 and the body 104 can be a monolithic component that can be machined from a single piece of material such as surgical grade stainless steel or titanium. As such, different sizes of sleeves can be available to allow a single sized base 202 and first taper 112 to be used for a variety of stems that can be different sizes.

For example, the sleeve 206 can be selected from the plurality of sleeves to correspond to stems of different sizes. For instance, the stem 116 used for a female may be smaller than a stem used for a male. Thus, the second taper 114 of the two stems can be different sizes. As a result, the surgeon can select the proper sleeve 206 to correspond with the stem 116 selected for a given patient, while using a body 104 and base 202 having a unitary construction.

The base 202 can be detachable. For instance, as discussed herein, the base 202 can be held to the body 104 using the lock 110. In addition, the base 202 can be selected from a plurality of bases. For example, when the base 202 is detachable from the body 104, the base 202 can be selected from the plurality of bases to correspond to a plurality of different stem sizes. For instance, the stem used for a female may be smaller than a stem used for a male. Thus, the second taper 114 of the two stems can be different sizes. As a result, the surgeon can select the proper base 202 to correspond with the stem 116 selected for a given patient.

Figure 3:
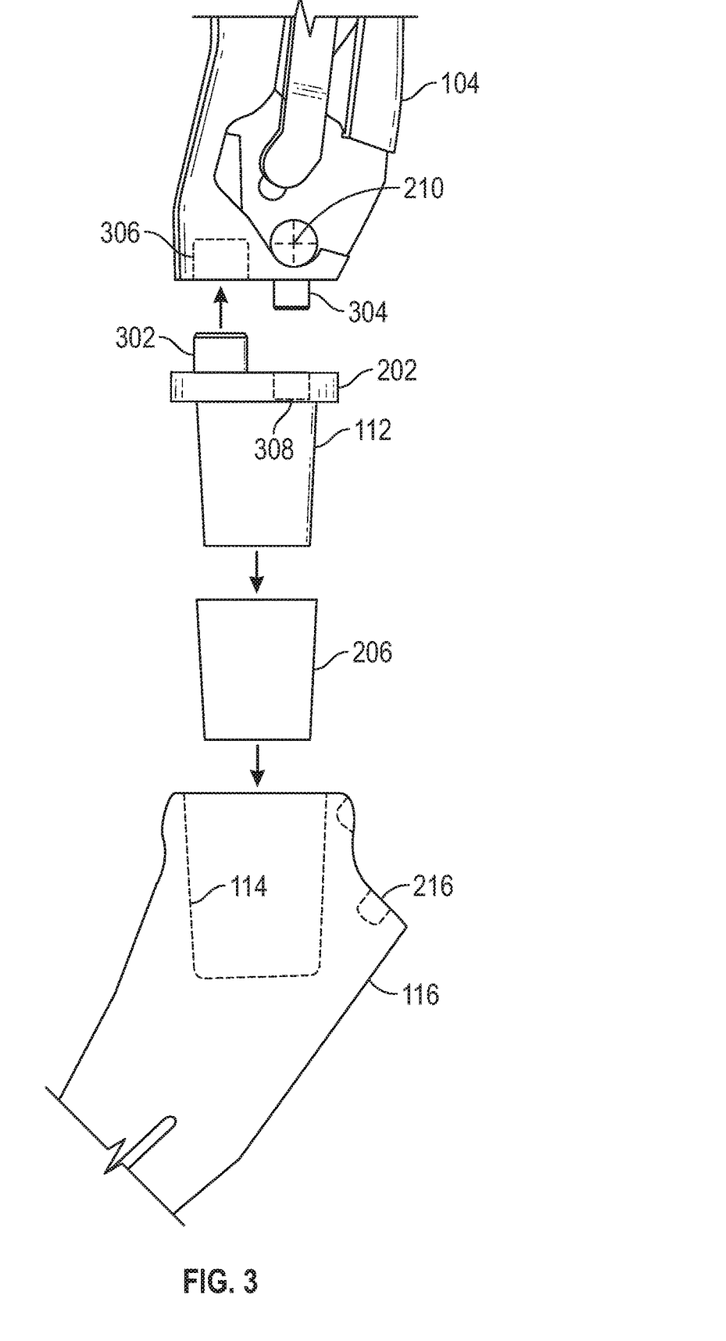
FIG. 3 shows an example of a partial exploded assembly of an impactor-extractor in accordance with at least one example of the present disclosure.

FIG. 3 shows an example of the base 202 being detachable. As shown in FIG. 3, the base 202 can include a first peg 302 and the body 104 can include a second peg 304. To assemble the impactor-extractor 100, the first peg 302 can be inserted into a first hole 306 and the second peg 304 can be inserted into a second hole 308. The first peg 302 and the second peg 304 can provide lateral stability for the base 202. In addition, the first peg 302 and the second peg 304 can be tapered or otherwise sized to form a compression fit with the first hole 306 and the second hole 308 to secure the base 202 to the body 104. FIG. 3 also shows the sleeve 206 can be installed over the first taper 112 and inserted into the second taper 114.

Returning to FIG. 2, the lever 106 can be pivotable about a pivot point 103 as indicated by arrow 208. The lever 106 can be connected to the lock 110 by linkages 107 and 108 such that movement of the lever 106 about the pivot point 103, as indicated by arrow 208, can cause movement of the lock 110 about a point 210 as indicated by arrow 212. For example, movement of the lever 106 from a first position can cause the lock 110 to pivot about the point 210 to secure the stem 116 to the impactor-extractor 100. Movement of the lever 106 from a second position back to the first position can cause the lock 110 to pivot about the point 210 and release the stem 116 from the impactor-extractor 100. As shown in FIG. 2, the lock 110 can include an extension 214 that can rest in an indentation 216 located in the stem 116. When the first taper 112 is inserted in the second taper 114, with the sleeve 206 in between, and the extension 214 is resting within the indentation 216, movement of the stem 116 can be restricted such that the stem 116 is securely connected to the impactor-extractor 100.

The linkage 108 can rest within the body 104. For example, the linkage 108 can rest in a notch 218 defined by the body 104. The linkage 108 resting in the notch 218 can allow the surgeon to grip the body 104 without causing binding between the linkage 108 and the body 104. The notch 218 cart be sized to allow the linkage 108 to move about a plane defined by a surface of the linkage 108 or the body 104.

As shown in FIG. 2, the stem 116 can have an axis 220. The body 104 can have a curved profile. The curved profile can result in the axis 220 of the stem 116 being offset from the impact head 102 while maintaining the axis 220 normal to the proximal surface 118 and the distal surface 120. By having the axis 220 normal to the surfaces of the impact head 102, impact forces imparted upon the impact head 102 can be transferred in a direction of the axis 220. Stated another way, the curved profile of the body 104 can allow the impactor-extractor 100 to position the stem 116 with the impact head 102 offset from the stem 116 such that an impact force on the impact head 102 can be transferred in a general direction the stem 116 is to be inserted or extracted.

Figure 4:
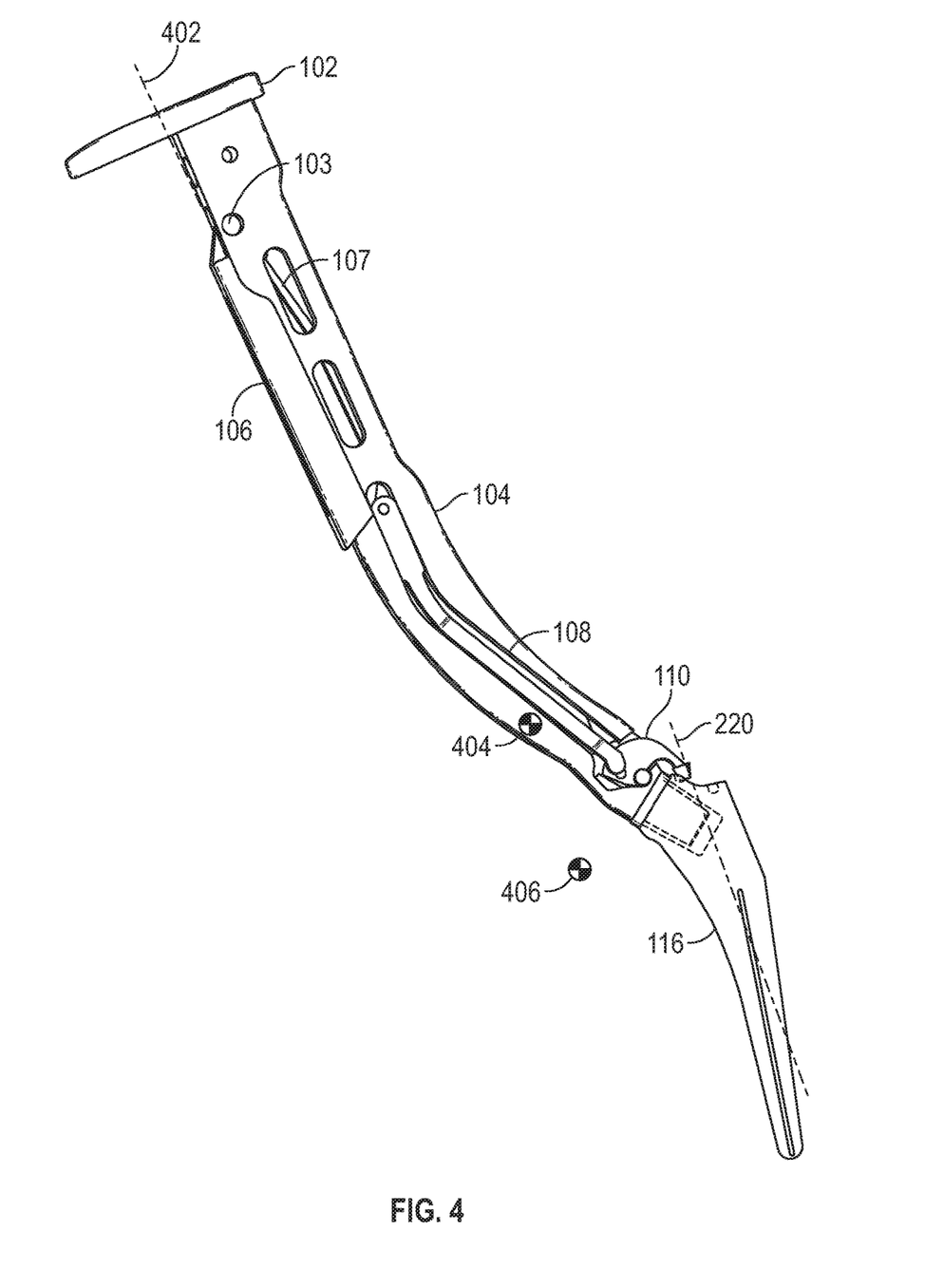
FIG. 4 shows an example of an impactor-extractor in accordance with at least one example of the present disclosure.

In addition, the distal surface 120 and the proximal surface 118 can be angled relative to the axis 220. Depending on the degree of the curvature of the body 104, a natural twisting moment could develop on the stem 116 when the impact head 102 is impacted due to the distance between the impact head 102 and the center of mass of the impactor-extractor 100 and the stem 116. For example, a curved profile of the body 104 that results in an offset of, for example, six inches of the impact head 102 and the center of mass of the impactor-extractor 100 and the stem 116 can result in a larger twisting moment than a one inch offset. To help counter the larger twisting moment the proximal surface 118 and the distal surface 120 can be angled as shown in FIG. 4 such that a line of action 402 can intersect or otherwise be directed closer to a center of mass 404 of the impactor-extractor 100 and stem 116. While FIG. 4 shows a location of the center of mass 404, it is understood that the center of mass 404 can be located elsewhere. For example, the size, shape, and mass, of the stem 116 attached to the impactor-extractor 100 can easily shift the center of mass 404. Also, while FIG. 4 shows the center of mass 404 being a point on the impactor-extractor 100, the center of mass 404 can be any point in space such as, for example, point 406.

Figure 5:
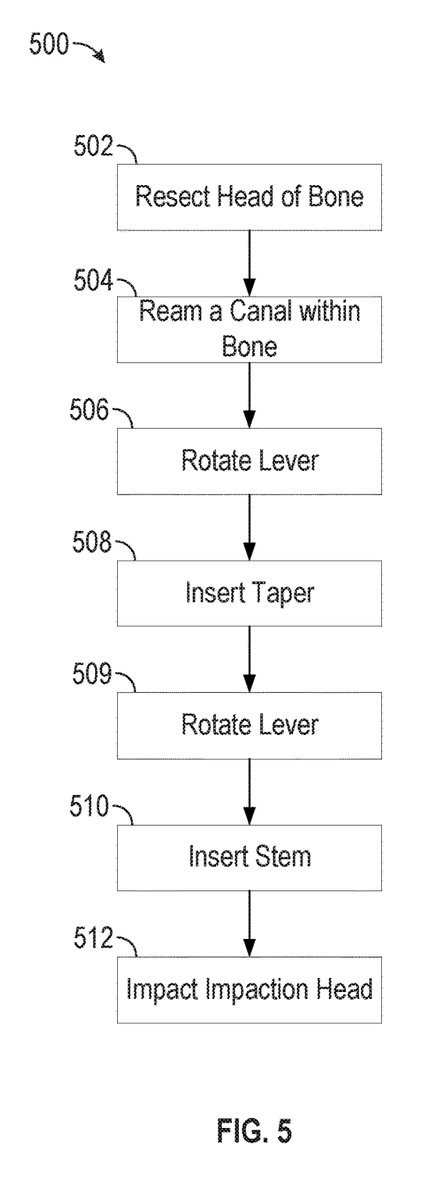
FIG. 5 shows an example method for installing a stem in accordance with at least one example of the present disclosure.

FIG. 5 shows a flowchart for a method 500 of implanting a stem, such as the stem 116, into a patient. For example, the method 500 can be used to install a temporary stem used for measurement purposes or to install a permanent stem as part of a joint replacement procedure. The method 500 can begin at stage 502 where a head of a bone of a patient can be resected. Non-limiting examples of the bone and head of the bone can include the femur and femoral head and the humerus and humeral head.

Once the head has been resected, the method 500 can proceed to stage 504 where a canal within the bone can be reamed. For example, after removing a femoral head from a femur, the femoral canal can be reamed to prepare the femur to accept the stem 116.

From stage 504, the method 500 can proceed to stage 506 where the lever 106 can be repositioned. For example, the lever 106 can be rotated from a first position on the body 104. The repositioning of the lever 106 can cause the lock 110 to pivot about the point 210 such that the lock 110 rotates upward relative to the base 202.

From stage 506, the method 500 can proceed to stage 508 where the first taper 112 can be inserted into the second taper 114. At stage 508 the sleeve 206 also can be selected and installed on the first taper 112 as described herein. Furthermore, the first taper 112 can be selected as described herein for the stem 116.

From stage 508, the method 500 can proceed to stage 509 where the lever 106 can be repositioned. For example, the lever 106 can be rotated from a first position on the body 104. The repositioning of the lever 106 can cause the lock 110 to pivot about the point 210 such that the lock 110 engages the stem 116 as described herein.

From stage 509, the method 500 can proceed to stage 510 where the stem 116 can be inserted into the canal. For example, once the stem 116 is connected to the impactor-extractor 100, the surgeon can insert the stem 116 into the reamed canal and position the stem as appropriate for the patient. Once the stem 116 is properly positioned within the canal the method 500 can proceed to stage 512 where the distal surface 120 can be impacted to seat the stem 116 into the canal.

Figure 6:
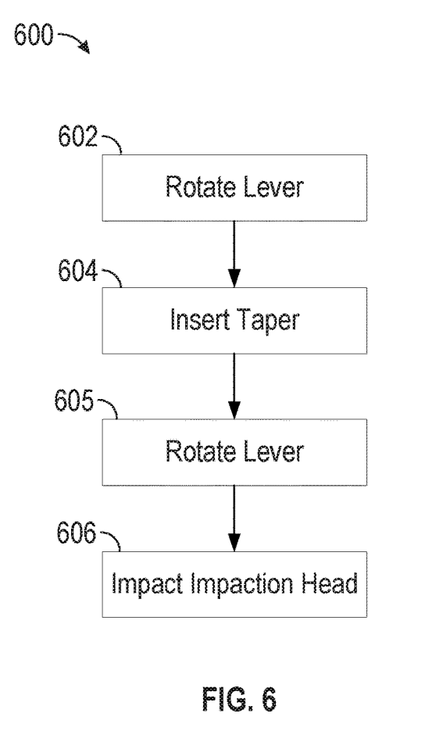
FIG. 6 shows an example method for extracting a stem in accordance with at least one example of the present disclosure.

FIG. 6 shows a flowchart for a method 600 of extracting the stem 116 from a patient. For example, the method 600 could be implemented to remove a temporary stem or during a revision of a joint replacement. The method 600 can begin at stage 602 where the lever 106 can be repositioned. For example, the lever 106 can be rotated from a first position relative to the body 104 to a second position relative to the body 104. The repositioning of the lever 106 can cause the lock 110 to pivot about the point 210 such that the lock 110 rotates upward relative to the base 202.

From stage 602, the method 600 can proceed to stage 604 where the first taper 112 can be inserted into the second taper 114. At stage 604 the sleeve 206 also can be selected and installed on the first taper 112 as described herein. Furthermore, the first taper 112 can be selected as described herein for the stem 116.

From stage 604, the method 600 can proceed to stage 605 where the lever 106 can be repositioned. For example, the lever 106 can be rotated from the second position relative to the body 104 to the first position relative to the body 104. The repositioning of the lever 106 can cause the lock 110 to pivot about the point 210 such that the lock 110 engages the stem 116 as described herein.

From stage 605, the method 600 can proceed to stage 606 where the proximal surface 118 can be impacted to unseat the stem 116 from the canal. Once the stem 116 has been unseated from the canal, the stem 116 can be removed from the bone.

The various components of the impactor-extractor 100 can be manufactured from a variety of materials and using a variety of manufacturing techniques. For example, the impact head 102, the body 104, the base 202, and the first taper 112 can be manufactured from metals, polymers, and ceramics. The impactor-extractor 100 can be first cast into a rough form and then machined into a final form. In addition, the impactor-extractor 100 can be machined from a solid billet.

The lever 106 can be manufactured from metals, polymers, and ceramics. The lever 106 can be machined, injection molded, over-molded, etc. The lever 106 can be of unitary construction or can be multiple pieces. For example, the lever 106 can include two halves that are snapped together to secure the lever 106 to the body 104.

The sleeve 206 can be manufactured from a polymer or ceramic. The sleeve 206 can be injection molded, over molded, etc. The lock 110 can be manufactured from metals, polymers, and ceramics. The lock 110 can be injection molded, cast, machined, etc.

It will be readily understood to those skilled in the art that various other changes in the details, material, and arrangements of the parts and method stages which have been described and illustrated in order to explain the nature of the inventive subject matter may be made without departing from the principles and scope of the inventive subject matter as expressed in the subjoined claims.

What is claimed is:

1. An impactor-extractor for inserting or extracting a stem of a prosthesis into or from a bone, the impactor-extractor comprising:
   a body having a first end and a second end, the body including an impact head located at the first end of the body;

a lever connected to the body, the lever pivotable about a first pivot point;

a base located at the second end of the body, the base including a first taper connector sized to mate with a second taper connector of the stem;

a lock located at and pivotable about a second pivot point proximate the second end, the lock including an extension configured to secure the stem to the first taper connector; and a linkage connecting the lever and the lock, wherein movement of the lever in a first direction causes the lock to pivot about the second pivot point and the extension to engage the stem, and wherein movement of the lever in a second direction causes the lock to pivot about the second pivot point and the extension to disengage the stem.

2. The impactor-extractor of claim 1, wherein the first taper connector is a male taper and the second taper connector is a female taper.

3. The impactor-extractor of claim 1, wherein the first taper connector s a female taper and the second taper connector is a male taper.

4. The impactor-extractor of claim 1, wherein the extension includes a protrusion sized to be received within an indentation formed in the stem.

5. The impactor-extractor of any one of or any combination of claims 1-4, further comprising a sleeve sized to fit over the first taper and into the second taper.

6. The impactor-extractor of claim 5, wherein the sleeve is selected from a plurality of sleeves, each of the plurality of sleeves configured to mate with stems of differing sizes.

7. The impactor-extractor of claim 1, wherein the base is selected from a plurality of bases, each of the plurality of bases configured to mate with stems of differing sizes.

8. The impactor-extractor of claim 1, wherein the linkage rests within the body.

9. The impactor-extractor of claim 1, wherein the impact head includes:

a proximal surface for receiving an impaction force to seat the stem within a canal of the bone; and a distal surface for receiving an extraction force to unseat the stem from the canal of the bone.

10. The impactor-extractor of claim 1, wherein the base includes a baseplate located between the first taper and the body, the baseplate configured to disperse an impaction force over a surface of the stein.

11. The impactor-extractor of claim 10, further comprising a sleeve sized to fit over the first taper and a contact surface of the baseplate and into the second taper.

12. An impactor-extractor for inserting or extracting a stem of a prosthesis into or from a bone, the impactor-extractor comprising:

a body having a first end and a second end, the body including an impact head located at the first end of the body, the body having a curved profile such that a distal surface of the impact head is offset from the second end and normal to an axis of the stem;

a lever connected to the body, the lever pivotable about a first pivot point;

a base located at the second end of the body, the base including a first taper sized to be received by a second taper of the stem;

a lock located at and pivotable about a second pivot point proximate the second end, the lock including a protrusion sized to be received within an indentation formed in the stem; and a linkage connecting the lever and the lock, wherein movement of the lever in a first direction causes the lock to pivot about the second pivot point and the protrusion to engage the indentation, and movement of the lever in a second direction causes the lock to pivot about the second pivot point and the protrusion to disengage the indentation.

13. The impactor-extractor of claim 12, wherein the first taper connector is a male taper and the second taper connector is a female taper.

14. The impactor-extractor of claim 12, wherein the first taper connector is a female taper and the second taper connector is a male taper.

15. The impactor-extractor of claim 12, wherein the base includes a baseplate located between the first taper and the body, the baseplate configured to disperse an impaction force over a surface of the stem.

16. A method of implanting a stem of a prosthesis into a bone of a patient, the method comprising:

resecting a head of the bone;

reaming a canal within the bone;

inserting a first taper of an impactor-extractor into a second taper of the stem;

rotating a lever about a first pivot point from a first position on a body of the impactor-extractor to a second position on the body of the impactor-extractor, wherein rotating the lever causes a lock to pivot about a second pivot point located proximate the first taper such that an extension of the lock engages the stem, inserting the stem into the canal within the bone; and impacting a distal surface of an impaction head of the body to seat the stem into the canal.

17. The method of claim 16, further comprising extracting the stem from the canal.

18. The method of claim 17, wherein extracting the stem from the canal includes:

inserting the first taper of the impactor-extractor into the second taper of the stem;

rotating the lever from the first position on the body to the second position on the body, wherein rotating the lever causes the lock to pivot about the second pivot point located proximate the first taper such that the extension of the lock engages the stem; and impacting a proximal surface of the impaction head of the body to unseat the stem from the canal.

19. The method of claim 16, wherein the first taper connector is a male taper and the second taper connector is a female taper.

20. The method of claim 16, wherein the first taper connector is a female taper and the second taper connector is a male taper.

* * * * *

UNITED STATES PATENT AND TRADEMARK OFFICE
CERTIFICATE OF CORRECTION

| | |
|---|---|
| PATENT NO. | : 10,398,569 B2 |
| APPLICATION NO. | : 15/617410 |
| DATED | : September 3, 2019 |
| INVENTOR(S) | : Nicolas V. Jaumard |

It is certified that error appears in the above-identified patent and that said Letters Patent is hereby corrected as shown below:

In the Claims

Column 9, Line 22, Claim 3, delete "s" and insert --is--

Column 9, Line 46, Claim 10, delete "stein." and insert --stem.-- therefor

Column 10, Line 44, Claim 18, delete "stern;" and insert --stem;-- therefor

Signed and Sealed this
Thirty-first Day of March, 2020

Andrei Iancu
*Director of the United States Patent and Trademark Office*